US00RE39107E

(19) United States
(12) Reissued Patent
Shaw

(10) Patent Number: US RE39,107 E
(45) Date of Reissued Patent: May 23, 2006

(54) CAP OPERATED RETRACTABLE MEDICAL DEVICE

(75) Inventor: Thomas J. Shaw, Little Elm, TX (US)

(73) Assignee: Retractable Technologies, Inc., Little Elm, TX (US)

(21) Appl. No.: 09/665,634

(22) Filed: Sep. 19, 2000

Related U.S. Patent Documents

Reissue of:
(64) Patent No.: 5,810,775
Issued: Sep. 22, 1998
Appl. No.: 08/862,849
Filed: May 23, 1997

(51) Int. Cl.
*A61M 5/00* (2006.01)

(52) U.S. Cl. ..... 604/110; 604/195; 600/576
(58) Field of Classification Search ..... 604/110, 604/195, 192, 198, 187, 263, 181, 403, 411–413; 222/325; 215/234–236, 238, 240, 354
See application file for complete search history.

(56) References Cited

U.S. PATENT DOCUMENTS

| | | | |
|---|---|---|---|
| 4,562,844 | A | 1/1986 | Carpenter et al. |
| 4,747,831 | A | 5/1988 | Kulli |
| 4,813,426 | A | 3/1989 | Haber et al. |
| 4,838,863 | A | 6/1989 | Allard et al. |
| 4,838,869 | A | 6/1989 | Allard et al. |
| 4,841,985 | A | 6/1989 | Wanamaker |
| 4,850,374 | A | 7/1989 | Diaz-Ramos |
| 4,904,242 | A | 2/1990 | Kulli |
| 4,932,418 | A | 6/1990 | Coburn |
| 4,947,863 | A | 8/1990 | Haber et al. |
| 4,966,593 | A | 10/1990 | Lennox |
| 4,984,580 | A | 1/1991 | Wanamaker |
| 4,988,339 | A | 1/1991 | Vadher |
| 4,994,034 | A | 2/1991 | Botich et al. |
| 5,019,044 | A | 5/1991 | Tsao |
| 5,030,209 | A | 7/1991 | Wanderer et al. |
| 5,046,508 | A | 9/1991 | Weissler |
| 5,049,133 | A | 9/1991 | Pascual |
| 5,053,010 | A | 10/1991 | McGary et al. |
| 5,064,419 | A | 11/1991 | Gaarde |

(Continued)

FOREIGN PATENT DOCUMENTS

| | | | |
|---|---|---|---|
| EP | 0 539 634 | A1 | 5/1993 |
| JP | H02-502076 | A | 7/1990 |
| JP | H03-504209 | A | 9/1991 |
| JP | H07-246196 | A | 9/1995 |
| WO | WO 95/08358 | A1 | 3/1995 |
| WO | WO 95/16389 | A1 | 6/1995 |
| WO | WO 96/05879 | A1 | 2/1996 |
| WO | WO 98/48869 | A1 | 11/1998 |
| WO | WO 98/52630 | A1 | 11/1998 |

*Primary Examiner*—Cris L. Rodriguez
(74) *Attorney, Agent, or Firm*—Locke Liddell & Sapp LLP

(57) ABSTRACT

A cap operated retractable medical device has an outer body with a hingedly connected outer cap which moves between an open and a closed position. The device is used as a blood sampler with a conventional collection tube normally used in such devices. A movable member is entirely enclosed within the outer body. A sliding interference or friction fit holds a retraction body within the mouth of the movable member and also holds the front end of the movable member within the outer body positioned within the retraction body adjacent a stop. A double ended needle is installed in the retraction body. Camming protrusions on the cap engage the back of the movable member to move it forward as the cap is closed thereby triggering retraction of the retraction body and its double ended needle entirely within the outer body. Once the cap is closed with the double ended needle safely inside, the device can be safely handled. The device is compact. It can be as short as the needles it will safely contain.

57 Claims, 5 Drawing Sheets

U.S. PATENT DOCUMENTS 5,067,490 A 11/1991 Haber
5,067,945 A 11/1991 Ryan et al.
5,070,885 A 12/1991 Banaldo
5,084,018 A 1/1992 Tsao
5,085,640 A * 2/1992 Gibbs ..... 604/110
5,086,780 A * 2/1992 Schmitt ..... 600/576
5,104,378 A 4/1992 Haber et al.
5,112,316 A 5/1992 Venturini
5,114,410 A 5/1992 Batlle
5,120,311 A 6/1992 Sagstetter et al.
5,125,414 A 6/1992 Dysarz
5,180,369 A 1/1993 Dysarz
5,180,370 A 1/1993 Gillespie
5,188,599 A 2/1993 Botich et al.
5,188,613 A 2/1993 Shaw
5,193,552 A 3/1993 Columbus et al.
5,201,710 A 4/1993 Caselli
5,211,628 A 5/1993 Marshall
5,211,629 A 5/1993 Pressly et al.
5,219,333 A 6/1993 Sagstetter et al.
5,259,392 A 11/1993 Schmitt
5,336,187 A 8/1994 Terry et al.
5,344,407 A * 9/1994 Ryan ..... 604/192
5,385,551 A 1/1995 Shaw
5,389,076 A 2/1995 Shaw
5,395,337 A 3/1995 Clemens et al.
5,423,758 A 6/1995 Shaw
5,480,385 A 1/1996 Thorne et al.
5,578,011 A 11/1996 Shaw
5,613,952 A 3/1997 Pressly, Sr. et al.
5,616,135 A * 4/1997 Thorne et al. ..... 604/192
RE35,539 E 6/1997 Bonaldo
5,709,669 A 1/1998 Haining
5,769,826 A * 6/1998 Johnson et al. ..... 604/195
5,836,917 A 11/1998 Thorne et al.
6,024,710 A * 2/2000 Miller ..... 600/578
6,024,727 A 2/2000 Thorne et al.

* cited by examiner

CAP OPERATED RETRACTABLE MEDICAL DEVICE

Matter enclosed in heavy brackets [ ] appears in the original patent but forms no part of this reissue specification; matter printed in italics indicates the additions made by reissue.

BACKGROUND OF THE INVENTION

1. Field of the invention

The invention pertains to a retractable medical device which in the preferred embodiment is useful for collecting body fluids from a patient. It is primarily useful as a blood collection device.

2. Background of the Prior Art

Prevention of needle sticks has become a paramount concern of the healthcare industry because of serious and deadly risk factors associated with AIDS and other serious communication diseases. Blood collection devices utilize a needle inserted into a patient's vein so as to draw blood through the needle into an associated separate collection reservoir. Accidental needle sticks from previously used needles can occur during the fluid withdrawing process and subsequent handling and disposal operation. Until such used medical devices are destroyed, they remain potentially lethal.

Illustrative of the type of device used for blood sampling is a collection device sold under the trademark Vacutainer® by Becton Dickinson Corporation, which has been the conventional standard for this type of device. It has a tubular syringe-like body with a needle in the front end, part of which extends back into a tubular syringe-like shell. Part of the needle extends externally for punching the skin. An evacuated collection tube with a rubber stopper is placed into the open back of the syringe-like shell with the rubber stopper against the internal end of the needle. After the skin is punctured, the collection tube is pushed forward to cause the needle to enter the evacuated tube. Vacuum helps draw blood into the collecting tube. When a sufficient sample has been obtained, the collecting tube and the stopper are simply withdrawn from the tubular shell and sent to the laboratory. This particular device has a permanently extended needle and an opening in the back for the collection tube which remains open after the collection tube is removed, leaving small quantities of blood and an internally exposed needle.

Retractable medical devices which are used for collecting fluid samples from patients are known. While they offer retraction of the needle, they suffer from high manufacturing and assembly cost. They lack simplicity which results in a multiplicity of difficult to manufacture and assemble parts. An early example of such a device is Haber U.S. Pat. No. 4,813,426 which employs a mechanically translatable insert holding a double-ended needle. It has a position which compresses a spring portion of the holder. When buttons extending from opposite sides of the outer tube are compressed, the needle carrier can be mechanically moved to the position of us or to a rearward safe position. Allard U.S. Pat. No. 4,838,863 describes a spring loaded double ended needle carrier in a T-shaped housing having an opening behind for the sample tube. The needle holder is locked in a use position with a removable pin which is withdrawn to retract the needle. Alternately, breakable tabs on the needle holder extend laterally under a shelf with pins which may be pushed down when the sample tube is inserted to fracture the breakable tabs thereby releasing the needle holder which is withdrawn into the interior as the sample tube is removed. Subsequently, a cap is provided to close the back. Allard does not explain how one could assemble the device without making the outer body in two or more pieces.

In addition, a number of devices attach the double ended needle to a partially withdrawable plunger with an opening in back for the sample tube. Shaw U.S. Pat. No. 5,423,758 discloses a tubular outer body with a partially removable plunger. The plunger has a separable needle holding portion for a double ended needle and an opening in the back of the plunger for a sample tube. It utilizes a two position end cap from which the sample tube extends. The plunger is used to position and retract the needle assembly.

By in large, the prior art fails to take into account the need for a single one-handed required and controlled action that will simultaneously close the back of the main body of the device and initiate retraction of the exposed needle after the sample tube is removed. If the inner needle which punctures the collection tube is not covered with a rubber sheath, blood will continue to flow into the device. This blood provides a source of contamination during subsequent handling of the device. If the internal needle is covered with a rubber sheath to prevent the blood from continuing to flow after the collection tube is removed, the rubber sheath serves to hide a sharp needle which can result in unintended punctures. Since the sheathed needle looks safe, people tend to put their finger into the open end without thinking. Even if a cap were to be provided, it use requires a separate operation and it is easy to forget or simply fail to use it. Consequently, an improvement in safety is possible with a device that caps the back of the device while it is retracting.

SUMMARY OF THE INVENTION

The invention is a retractable medical device in the form of a blood sampler which can be operated by one hand without removing the device from the patient after one or more collection tubes are filled. While one hand holds a gauze pad over the puncture site, the other hand is used to manipulate a cap hingedly connected to the back of the device. As the cap is moved to the closed position, it moves a movable member forward releasing a retraction body with the needle which is retracted entirely within the walls of the now closed body. Once retracted, the sharp double ended needle is confined and cannot be used. Safety is assured because the act of closing the cap is the same act which causes retraction of the needle. It is the only way retraction can take place.

The cap operated retractable medical device includes a long thin walled tubular outer body having a back end with an opening and a front end which incorporates a centered hub which provides an opening for a needle holder. A long thin walled tubular movable member closely fits entirely within the outer body. The movable member has a back end with an opening and a front portion wherein the front portion has a radially enlarged inner surface and an outer surface. A retraction body having a disk-like laterally extending wall with an outwardly facing edge is releasably held within the movable member at a forward position by means of cooperation between the radially enlarged inner surface of the front portion of the movable member and the outwardly facing edge.

A thickened or stepped in portion of the wall of the outer body is provided for a short distance behind the front wall. The hub, preferably in the form of an annular ring, serves as a stop for the retraction body spaced behind the front wall of the outer body. It also serves to hold the front end of the compression spring which is placed between the front wall of the outer body and the retraction body. The movable member is held in position within the outer body, with the retraction body adjacent the hub, by means of a tight area created between the outer surface of the movable member and the stepped in or thickened inside surface of the wall of the outer body near its front end. The retraction body carries a double ended needle.

A cap which is hinged at the back end of the outer body is selectively movable between an open position and a closed position relative to the opening of the back of the outer body. The cap includes a cam surface configured to engage the back end of the movable member inside the outer body and move it forward as the cap is moved to the closed position. Closing the cap causes the movable member to move forward while the retraction body is restrained by the hub in the outer body thereby releasing the retraction body from the movable member. A spring compressed under the retraction body expands to drive the retraction body and double ended needle backward within the movable member just as the cap is fully closed. Another stepped in portion of the wall of the movable member near the back end catches the retraction body before the needle behind the retraction body can reach the area of the cap.

The tight area between the outer surface of the movable member and the inner surface of the outer body near the front of the device is in the nature of an interference fit which still allows the movable member to go forward when the cap is closed. Since the forwardly extending needle of the blood sampler does not need to puncture a rubber seal as does a syringe, the retraction body and movable member do not have to resist large forces before releasing. The rearward facing portion of the needle in the device does have to puncture the seal of a collection tube, but since the retraction body is positioned against a hub or stop at the front of the outer body and cannot move forward, impaling the collection tube on the interior end of the needle cannot disassociate the retraction body from the movable member.

The needle holder is carried by the retraction body with the needle extended in both directions. In the assembled condition, the conjunction of the retraction body and the hub provide a convenient means for installing the already assembled needle holder and needle through the opening in the front wall of the outer body. The needle holder is threaded into a centrally located opening in the retraction body. The centrally located opening of the retraction body has a forwardly extending tubular wall which cooperates with the hub to confine the spring between the hub and the retraction body. Since the spring closely circumscribes the tubular wall of the retraction body, it serves to stabilize the retraction body so that it tends to move straight back without tilting during its retraction.

The cap has an outer rim larger than the opening at the back of the outer body and an inner rim containing one or more camming protrusions which cam the back of the movable member when the cap is closed. The inner rim preferably comprises two camming protrusions which are spaced apart and positioned to enter the opening when the cap is moving to the closed position. The protrusions are oppositely positioned along the inner rim about half way from the hinged connection. The protrusions actually contact the back of the movable member before the cap is closed and continue moving the movable member until retraction occurs just as the cap is becoming fully closed.

A fail-safe design is provided. The needle can only retract when the cap is closed. Since the cap is hinged to the device, it cannot be lost or misplaced. There is little chance of premature retraction since retraction can only be initiated by closing the cap. Even if retraction is forced by pushing the needle against a solid object, the needle does not come out of the body. Once the cap is closed to retract the needle, no special handling is required. A sound is made when the retraction occurs. The fact that the cap is closed together with the sound assures that the needle is no longer exposed, even without looking. An additional visual indication is also provided by the clear plastic walls of the outer body and movable member which enables the user to visually observe the extended spring that proves retraction has occurred.

The parts are fewer in number than other retractable devices comprising only an outer body which can be molded as one together with the cap, the movable member, the retraction body and the needle assembly. Due to the fact that the movable member is contained entirely within the outer body, a more compact device is made possible, limited in length only by the space required to enclose the double ended needle. The parts are suitable for fabrication in multiple cavity high speed plastic injection molding machines. No special materials are utilized apart from the usual plastic materials employed in the syringe industry.

Assembly is simplified by sliding interference fitting of the parts in a straight line direction. First the retraction body is inserted from the rear of the movable member and moved forward to fit within its mouth. The back end of the compression spring is placed over the tubular extension and into a spring groove of the retraction body while the outer end is dropped into a hub at the front of the outer body as the movable member is moved forward to compress the spring. Then the movable member is moved forward until the front end slidingly engages the stepped in portion of the outer body which creates a tight area where the movable member is held and the retraction body is positioned just above the hub which serves as a stop. The needle assembly is then screwed into the retraction body through the opening in the front wall of the outer body. A removable protective cap can be placed over the exposed needle until the device is ready for use.

DETAILED DESCRIPTION OF THE PREFERRED EMBODIMENT

Figure 1:
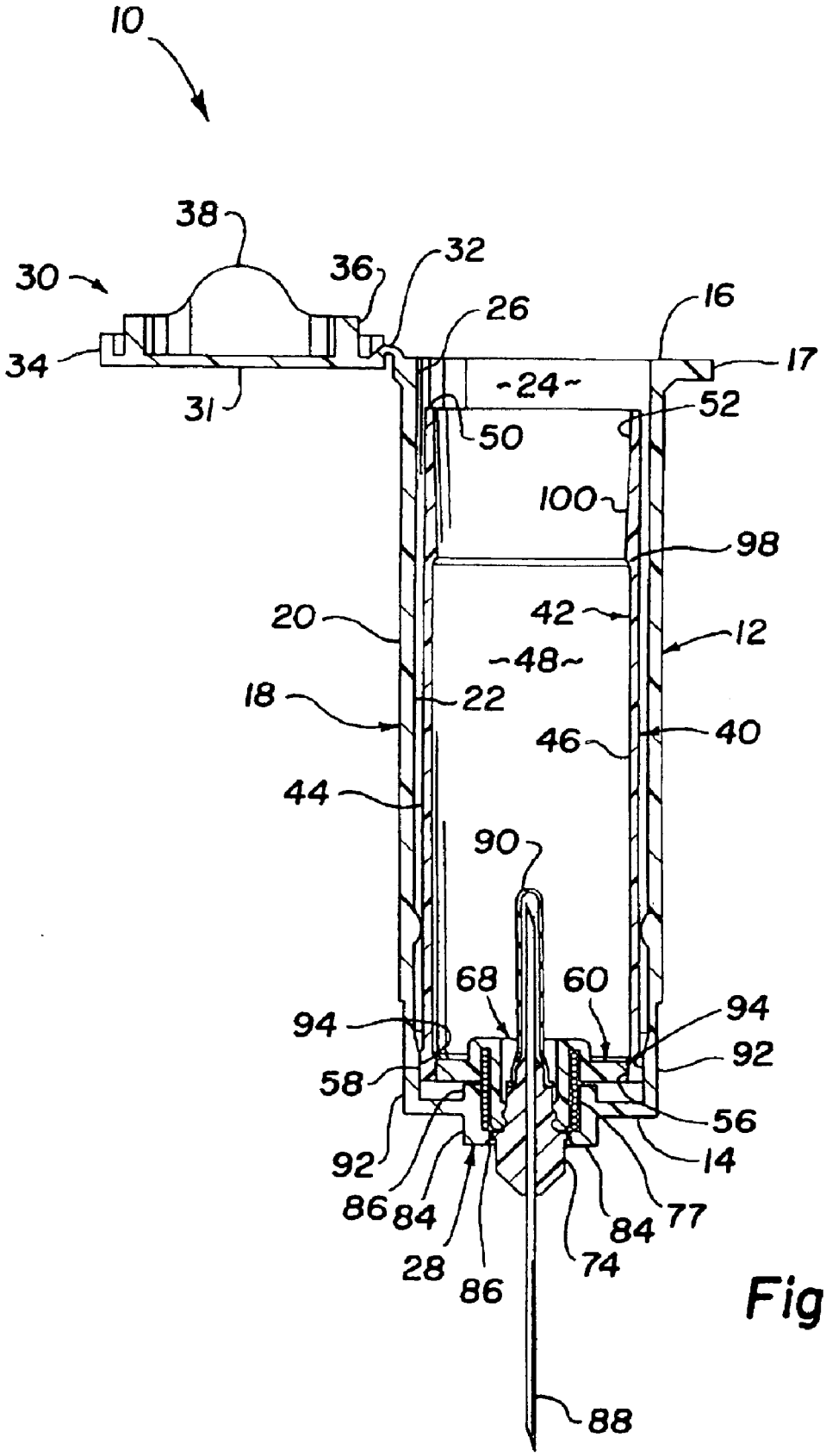
FIG. 1 is a cut-away view on the center line of the assembled medical device in the form of a blood collection sampling device in the ready-to-use position without the collection tube in place.

The medical device is generally referred to by the reference numeral 10 in FIG. 1. The device 10 is a fluid collection device, ore particularly a blood sampler. Device 10 has an elongated body 12 having a partially closed front 14 and an open back 16. There is an intermediate wall portion 18 connecting front 14 and back 16. Intermediate wall portion 18 has an outer wall surface 20 and an inner wall surface 22 which defines a hollow interior 24. Inner wall 22 together with open back 16 forms opening 26 at the back of outer body 12. A flange 17 is positioned at the back of outer body 12 to serve as a grip. It may be noted that flange 17 could be moved forward along body 12 if desired and is not necessarily located at the back of the body 12. In this regard, the forward direction is the direction in which the external needle 88 is extended.

Figure 3:
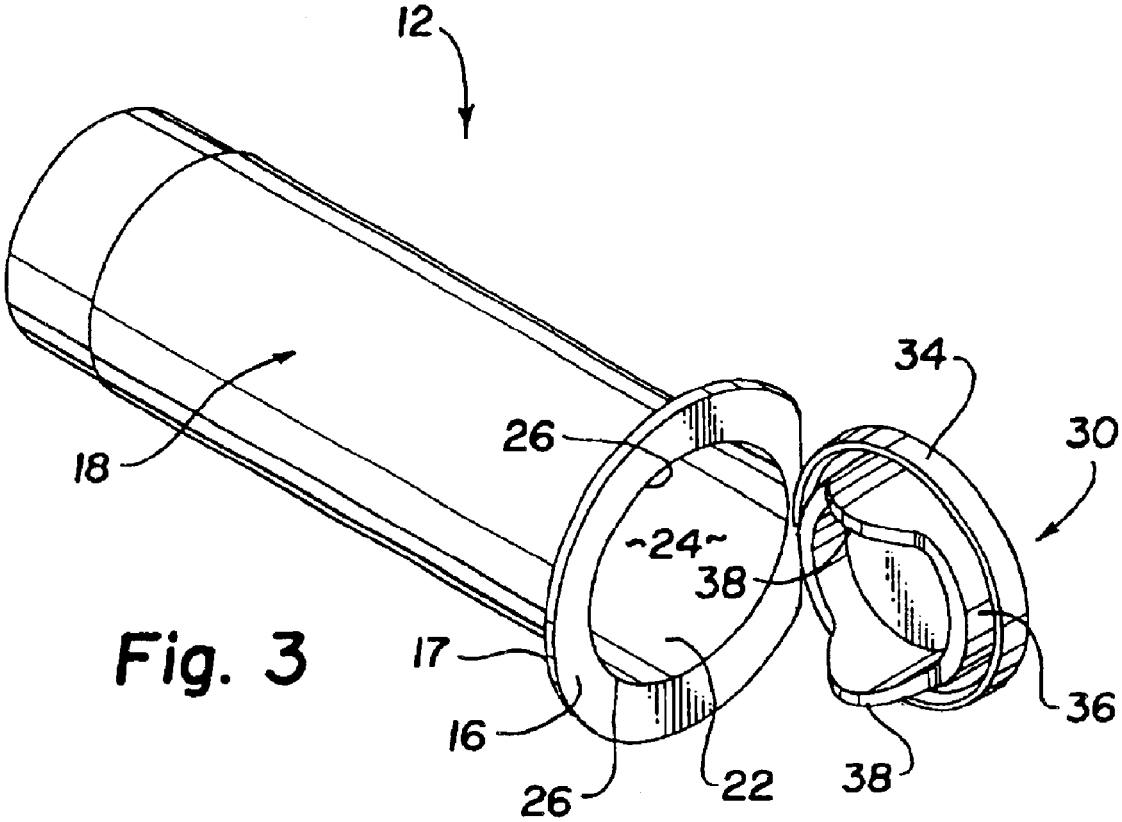
FIG. 3 is a perspective view of the outer tube and cap with the movable member in place in the position of use.
Figure 4:
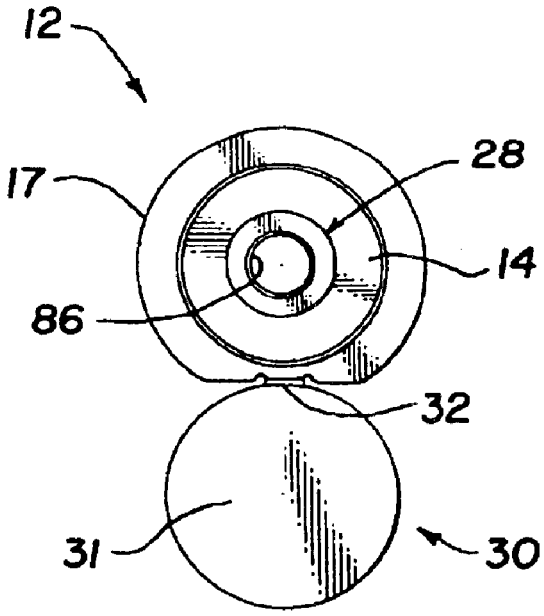
FIG. 4 is a front view of the medical device of FIGS. 1–3 showing the back of the cap when it is laid out level with the place of the flange at the back of the device.

FIG. 4 is a front view of elongated body 12 of FIG. 3 showing the flange 17 at the back and a hub 28 having a chamfered opening 86 in front. A selectively positionable cap designed to close opening 26 generally referred to by reference numeral 30 is hingedly connected at hinge 32 to back 16 of body 12. FIG. 4 shows cap 30 having a solid back 31. It is shown laid out fully from the position of FIG. 3.

Figure 2:
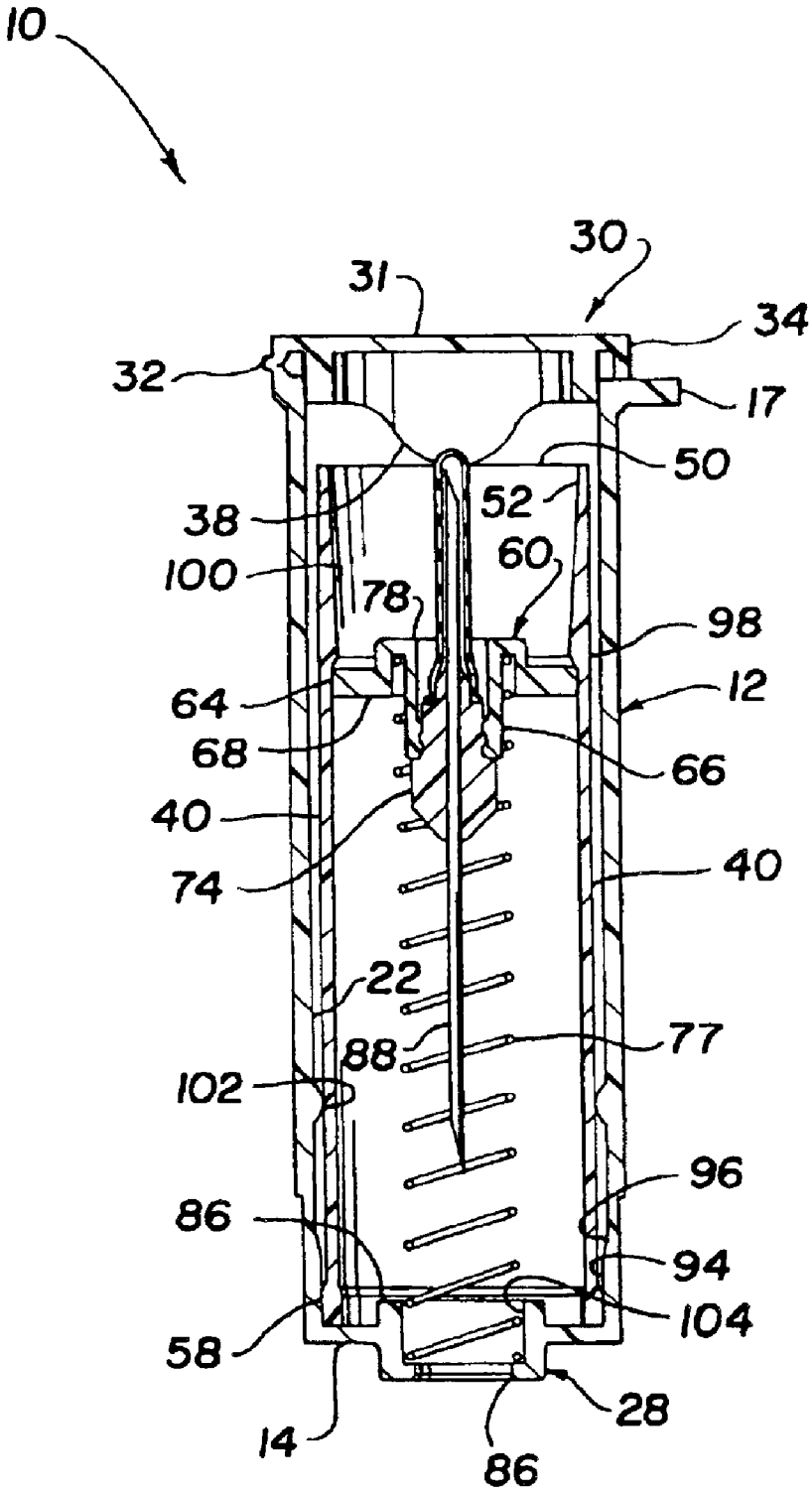
FIG. 2 is a view of the device of FIG. 1 after the cap has been moved from the open to the closed position thereby triggering retraction of the retractable member and closing the rear of the outer tube.

Cap 30 is positionable between an open position as shown in FIG. 1 and FIG. 3 and a closed position as shown in FIG. 2. The open position allows access to hollow interior 24 while the closed position blocks opening 26 from outside access. Cap 30 has an outer rim 34 larger than opening 26 in the back of outer body 12 and an inner rim 36 which constitutes a camming protrusion which moves through opening 26 when the cap is moving to the closed position. The preferred form of the inner rim is two camming protrusions 38 which are spaced apart and positioned to enter opening 26 close to inner wall surface 22 when the cap is moved to the closed position. The preferred protrusions are oppositely positioned along the inner rim about half way from hinged connection 32. Protrusions 38 could take different forms. As will be seen, they are designed to operate the movable member. FIG. 3 shows the orientation of body 12 as it would be placed above a patient's arm during use. The lobe of the protrusions of this preferred arrangement are not in the way of a conventional collection tube which will be inserted from the rear. The collection tube slides between the protrusions into opening 24. This means that cap 30 does not require an open position more open than a right angle with respect to back end 16. An additional advantage is that the cap closes more fully before it contacts the movable member and contacts it at opposite points which avoids any tendency to bind. The outer surface of inner rim 36 friction fits into opening 26 so that the cap stays closed.

An elongated movable member generally designated 40 in FIG. 1 is shorter than outer body 12 and is contained entirely therein. Movable member 40 is a long thin walled tubular member having a wall 42 with an external surface 44 and an internal surface 46. Wall 42 is configured to define the external surface 44 in close proximity to inner surface 22 of outer body 12. The wall and internal surface 46 defines a cavity 48 therethrough and an open back end 50 which serves as a contact surface for one or more camming protrusions 38 on cap 30. Open back end 50 defines an opening 52, which as will be seen, accepts a conventional evacuated collection tube with a rubber stopper in front, not shown in the Figures. The collection tube occupies most of cavity 48 and its closed back end extends some distance beyond back 16.

Figure 6:
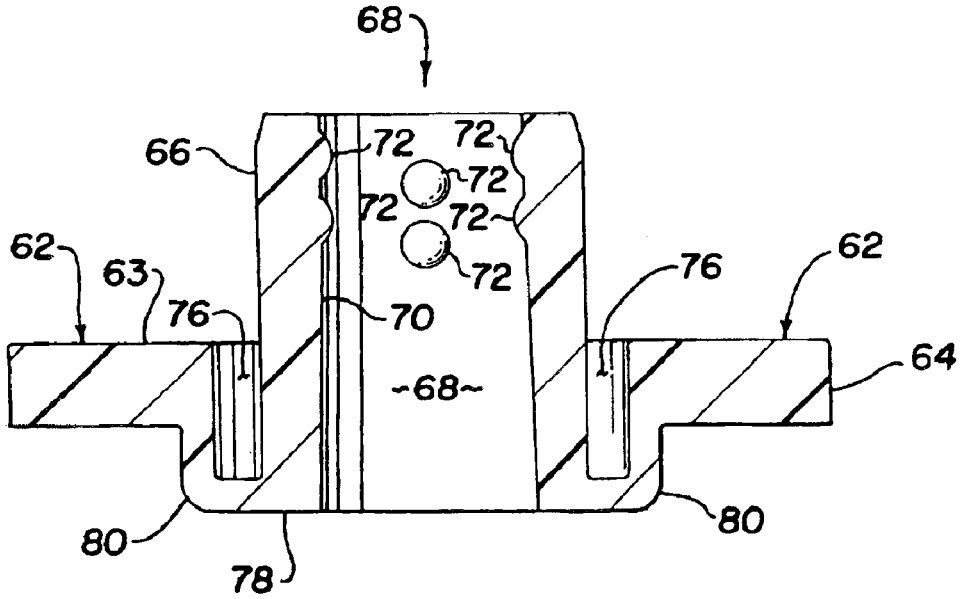
FIG. 6 is a view of the retraction body of FIG. 5 cut-away on the line 6—6 of FIG. 5.
Figure 7:
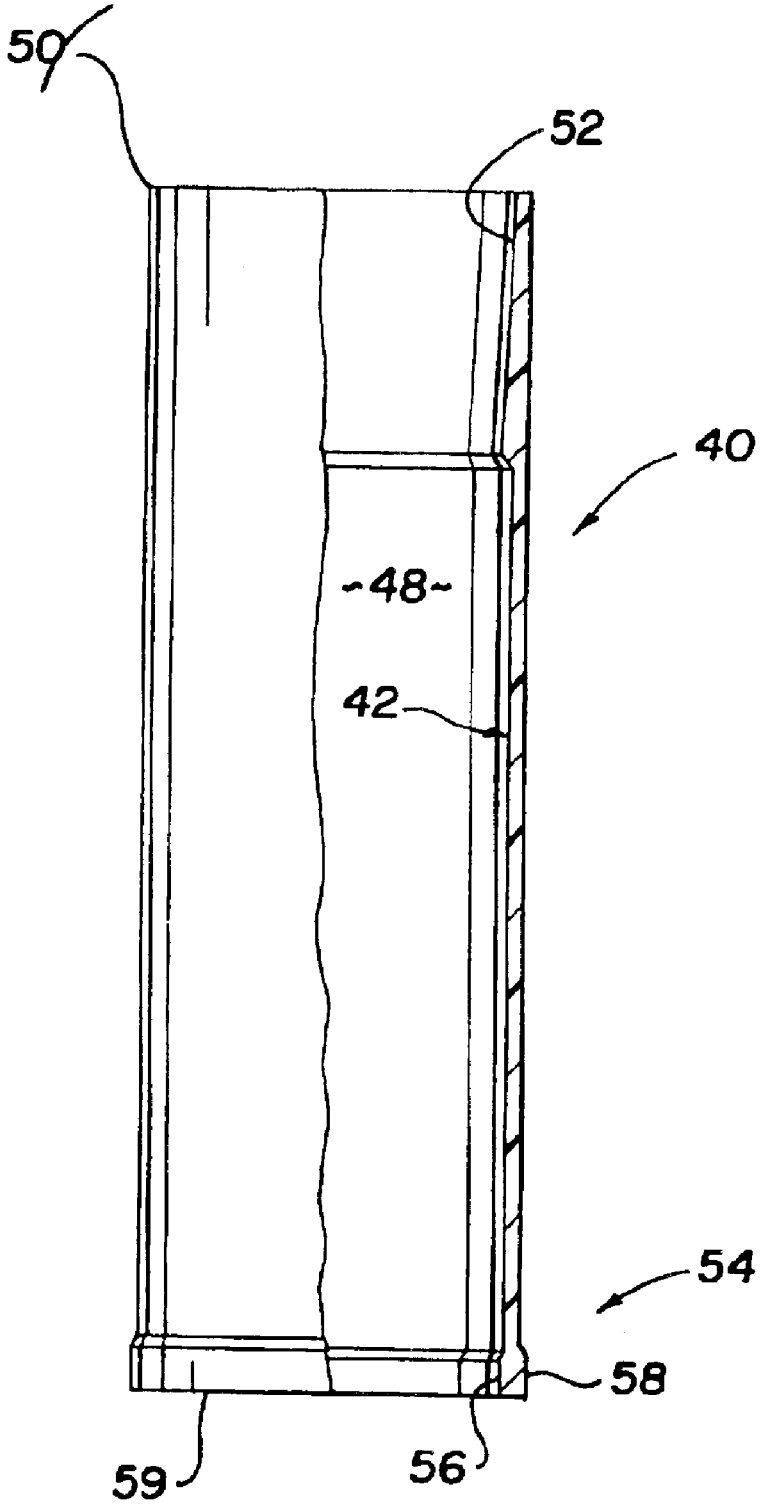
FIG. 7 is a partially cut-away view of the movable member showing preferred details of the wall structure.

Referring now to FIG. 7, movable member 40 has a front end portion 54 which preferably had a radially enlarged inner surface 56 and an outer surface 58 which may also be radially enlarged as shown. It has a front end 59. A retraction body 60 seen in FIGS. 5 and 6 is releasably held by movable member 40 at the radially enlarged inner surface 56 of front end portion 54.

Figure 5:
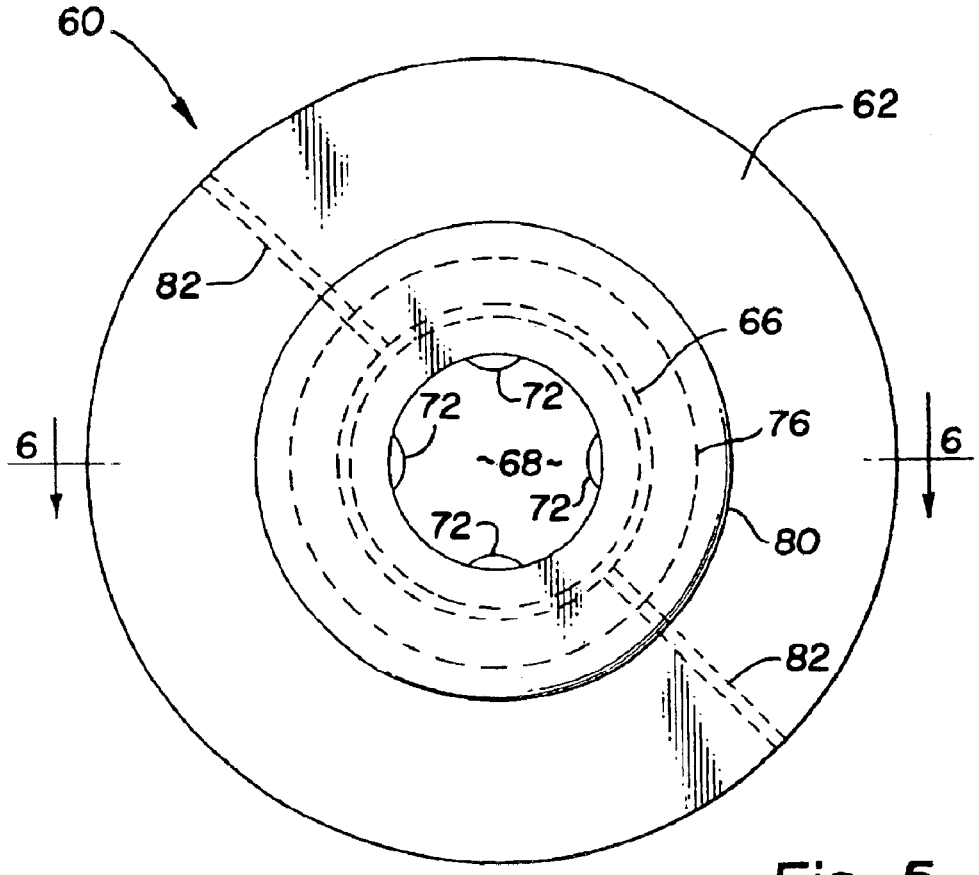
FIG. 5 is a plan view of the retraction body seen from behind looking forward towards the front of the device.

Retraction body 60 is best seen in FIGS. 5 and 6. Retraction body 60 has a laterally extending wall 62 in a discoid shape with an outwardly facing edge 64 which is held by the radially enlarged inner surface 56 of wall 42 as shown in FIG. 1. The radially enlarged surface 56 nee not be a continuous surface, although that is preferred. It could be radially enlarged sectors or lands which project inwardly from inner surface 46 sufficient to hold retraction body 60 during use. There is no need for a seal at edge 64.

Retraction body 60 further includes a forwardly extending tubular wall 66 having a centrally located opening 68 which extends longitudinally along the central axis of the assembled device. Longitudinally extending opening 68 has an inner wall surface 70 which may have threads or a plurality of angularly spaced sets of radial protrusions 72. Radial protrusions 72 can serve as a thread substitute for securing a threaded needle holder 74 best seen in FIGS. 1 and 2. A spring groove 76 is formed around tubular wall 66 to receive the end portion of a spring 77. The front of retraction body 60 is designated 78 as a transition zone which connects tubular wall 66 with laterally extending wall 62. An angular extension 80 between front 78 and wall 62 provides an offset for wall 62 behind front 78 in the vertical direction such that compressive force applied to edges 64 can cause flexing of angular extension 80. Angular extension 80 can act somewhat like a very stiff spring especially if radial slots 82 are provided at one or several locations through wall 62. Such slots are indicated schematically by dotted lines in FIG. 5 as radial slots 82. A number of such slots could divide discoid wall 62 into sectors which are slightly compressible toward the center, independently of each other. This could facilitate fitting retraction device 60 within front portion 54 of movable member 40.

Returning to FIGS. 1 and 2, it can be seen that hub 28 has a flanged wall portion 84 which extends forwardly from wall 14 and forms an opening 86 for threaded needle holder 74. In addition, wall portion 84 extends rearwardly behind front 14 to form a stop 86. Needle holder 74 has a portion which extends forwardly of hub 28 and a threaded portion behind which screws into opening 68 of retraction body 60. Double ended needle 88 is securely held extending forwardly and rearwardly from needle holder 74. A collapsible rubber sheath 90 sealingly covers the rearwardly extending portion of needles 88. It is designed to seal the flow passage through needle 80 after a collection tube is removed in preparation for collection of another sample in a second collection tube. Stop 86 constitutes a means for preventing forward movement of retraction body 60 which is spaced behind the back of front wall 14. Stop 86 is preferably an annular ring which is a rearward extension of wall 84 behind wall 14. Stop wall 86, together with the inwardly extending flanges of wall 84 which form opening 86, create a well for holding spring 77.

The radially enlarged surface 58 of front end portion 54 of movable member 40 is slidably held by a portion of inner surface 22 of outer body 12 at a location spaced behind partially closed front wall 14 of the outer body. Intermediate wall 18 has a thickened portion 92 which extends a short distance behind front wall 14. This creates an inner surface portion 94 which extends radially inwardly from inner surface 22 of intermediate wall 18. This creates a constricted area in a band around the inside of outer body 12 adjacent front wall 14. A smooth ramp 96 leads into thickened area 92 whereby movable member 40 can be moved forwardly until outer surface 58 slidably engages surface 94 thereby creating a tight area in a band between surfaces 58, 94 which holds movable member 40 in the position shown in FIG. 1. The tight area is a sliding interference fit between the front portion of the movable member and the inner surface of the outer tube. Alternately, thickened area 92 could be a plurality of angularly arranged land areas which engage portions of outer surface 58. A great degree of holding force is not needed since the front portion of needle 88 is primarily designed to puncture skin and it not normally used to pass through rubber stoppers commonly used in vials.

Thickened area 92 may be regarded as creating a stepped in portion on the inner surface of body 12 which cooperates with outer surface 58 of the front portion of the movable member to create the tight area whereby the movable member is held in its forward position shown in FIG. 1. The stepped surface creates a smaller diameter for a short distance behind front wall 14 which clamps radially enlarged outer surface 58 when the movable member is introduced through opening 26 and moved forward until the cooperating surfaces 58 and 94 slidingly engage. Some compressive force is directed around the mouth of member 40 toward retraction body 60 which is held inside. The forwardly extending tubular wall 66 in cooperation with hub 28 serves to confine biasing spring 77 between the hub and the retraction body. The flanged wall portion 84 forms the opening 86 for needle holder 74 which is smaller than the diameter of the spring. Flanged portion 84 thus supports the spring at its forward end. In its use position in FIG. 1, the surface 63 of retraction body 60 wall 62 lies closely adjacent to stop 86 A plurality of guide bumps 102 on wall surface 22 help stabilize and locate movable member 40 within outer body 12 as it moves.

Assembly of device 10 is simple and well suited for automated assembly. First retraction body 60 without the needle holder is pushed through the open back end of movable member and moved forward with a tool until cooperating edge 64 and inwardly facing surface 56 are engaged at the mouth of movable member 40. The back end of spring 77 is positioned circumscribing tubular wall 66 of retraction body 60 and the front of the movable member holding the retraction body and the spring are pushed into opening 26 at the back of outer body 12. The front end of spring 77 is seated into a well-like opening 104 within hub 28 at the front of the outer body. A tool may be inserted through opening 86 to serve as a guide for the spring as it moves forward and prevent lateral buckling of the spring as it is compressed. Movable member 40 is moved entirely within outer body 12 until the outwardly facing surface 58 engages the cooperating stepped in surface 94 and moved forward until surface 63 of the retraction body reaches stop 86. Threaded needle holder 74 together with needle 88 is then placed into opening 86 and turned to secure it in place in retraction body 60. Finally, a removable protective cap (not shown) is placed over the exposed portion of needle 88 and device 10 is ready for sterilization and packaging.

In operation, the cap operated retractable medical device is supplied as shown in FIG. 1 except that a conventional removable cap is placed over the extended needle with its back end frictionally held by the protruding portion of needle holder 74. The protective cap is removed and needle 88 is inserted into a vein. A conventional rubber stopper collection tube (not shown) is inserted into the open back of device 10 and pushed forward while holding device 10 until the rearwardly extending portion of needle 88 punctures the rubber stopper and the needle passes through rubber sheath 90. The outer tube is held while a blood sample is collected in the collection tube. When the collection tube is filled sufficiently, it is removed from device 10 and put down. Sheath 90 restricts further flow of blood. Typically, a gauze pad is placed over the patient's entry point with one hand and the other hand is used to grasp device 10 while manipulating cap 30 towards the closed position with the thumb of the other hand. Thus, retraction with one hand is possible before the needle is removed from the patient.

As cap 30 is pivoted into a blocking position with respect to the opening 26, protrusions 38 come in contact with back end 50. As the thumb pushed cap 30 further into cavity 24, movable member 40 moves forward along surface 94 toward front wall 14. An annular stop 86 prevents retraction body 60 from moving forward with movable member 40. Stop 86 disassociates retraction body 60 from the mouth of the movable member. Retraction body 60 is freed from front portion 54 of the movable member by relative movement between edge 64 and surface 56. When retraction body 60 comes free, spring 77 acting on retraction body 60 then drives retraction body 60 backward carrying needle 88 into outer body 12. Constriction 98 which constitutes a stepped in portion 100 of the wall of the movable member prevents retraction body from further rearward movement beyond the retracted position of FIG. 2. Cap 30 completely closes the back of the outer body 12 in a friction fit. Coil spring 77 which closely circumscribes the tubular wall 66 of retraction body 60 tends to stabilize the retraction body as it is retracting so that it moves straight back without tilting. In the retracted position of FIG. 2, the sharp needle points are entirely enclosed within outer body 12 and not accessible. The opening in hub 28 is too small to insert a finger and cap 30 prevents access from behind. Consequently, the danger from needle sticks during subsequent handling and disposal of this single use medical device are greatly reduced once the cap is closed. The device cannot be retracted without closing the cap. Once retracted, the device is not reusable without considerably effort.

In the best mode, it is anticipated that only about ⅛ of a pound needs to be generated by spring 77 in its fully compressed position since retraction body 60 is essentially free from restraint once it is dissociated from the mouth of the movable member. The outer body 12 in cap 30 can be molded as a single unit. Hinge 32 is preferably a so-called "living hinge" which is connected to the body 12 during the molding process. Body 12 would preferably come out of the mold with cap 30 in the orientation shown in FIG. 4.

What is claimed is:

1. A cap operated retractable medical device combination comprising:

a long thin walled tubular outer body having a back end with an opening and a front end which incorporates a centered hub;

an elongated movable member closely fitting entirely within the outer body, the movable member having a back end with an opening and a front end and front portion wherein the front portion has a radially enlarged inner surface and an outer surface;

a retraction body having a laterally extending wall with an outwardly facing edge, releasably held at a forward position with respect to the movable member by means of the radially enlarged inner surface of the front portion of the movable member;

the movable member being held in position with the retraction body adjacent the hub of the outer body by means of a tight area created between the outer surface of the front portion of the movable member and the inside surface of the wall of the outer body near its front end;

a cap hinged at the back end of the outer body and selectively movable between an open position and a closed position relative to the opening at the back end of the outer body, said cap having a cam surface confined to engage the back end of the movable member inside the outer body and move it forward as the cap is moved to the closed position; and whereby closing the cap causes the movable member to move forward while the retraction body is restrained by the hub in the outer body thereby releasing the retraction body from the movable member.

2. The combination of claim 1 wherein the wall of the tubular outer body has a portion of the wall behind the front end which is thickened to create a stepped portion on its inner surface which cooperates with the outer surface of the front portion of the movable member to create said tight area whereby the movable member is held in a forward position.

3. The combination of claim 2 wherein the outer surface of the front portion of the movable member is radially enlarged relative to the wall of the movable member to cooperate with the stepped portion on the inner surface of the outer body to create the tight area which holds the movable member in a forward position.

4. The combination of claim 2 wherein a rear portion of the wall of the movable member has an inner surface which is stepped inwardly to form a constriction which will catch the retraction body when it retracts and prevent it from escaping from the movable member.

5. The combination of claim 1 wherein the retraction body carries a needle holder with a needle extended through the front of the outer body.

6. The combination of claim 5 wherein the retraction body has a centrally located opening for securing said needle holder which can be installed from the front of the assembled device.

7. The combination of claim 6 wherein said centrally located opening is formed by a forwardly extending tubular wall which in cooperation with the hub serves to confine said biasing means between the hub and the retraction body.

8. The combination of claim 5 wherein said cap has an outer rim larger than the opening in the back of the outer body and an inner rim comprising two camming protrusions which are spaced apart and positioned to enter said opening when the cap is moved to the closed position.

9. The combination of claim 8 wherein said protrusions are oppositely positioned along the inner rim about half-way from the hinged connection.

10. A cap operated retractable medical device combination comprising:

an elongated outer body having a partially closed front, an open back and an intermediate wall portion connecting the front and back; wherein the intermediate wall portion has an inner surface that defines a hollow interior and an opening at the back;

a cap which is selectively positionable with respect to said opening between an open position which allows access to the hollow interior and a closed position which blocks said opening, said cap having a camming protrusion which moves through the opening when the cap is moving to the closed position;

an elongated movable member shorter than the outer body and contained therein, the movable member having a wall configured to define an external surface in close proximity to the inner surface of the wall of the outer body, an internal surface which defines a cavity therein and an open back end which serves as a control surface for the camming protrusion on said cap; and there is a front end portion of the movable member with radially enlarged inner and outer surfaces;

a retraction body releasably held by the movable member at the radially enlarged inner surface of the front end portion of the movable member;

the radially enlarged surface of the movable member being slidably held by a portion of the inner surface of the outer body at a location spaced behind the partially closed front of the outer body;

means for preventing forward movement of the retraction body and biasing means adapted to apply a retraction force to the retraction body; and whereby the retraction body may be released from the movable member for retracting by forward movement of the movable member caused by positioning the cap into the closed position while the retraction body is restrained by said means for preventing forward movement.

11. The combination of claim 10 wherein the retraction body carries a needle holder with a needle extended through the partially closed front.

12. The combination of claim 11 wherein the partially closed front comprises a hub centered along the longitudinal axis of the device.

13. The combination of claim 12 wherein the retraction body has a laterally extending discoid wall having an outer facing edge which is held by the radially enlarged inner surface of the front end portion of the movable member.

14. The combination of claim 13 wherein the retraction body has a centrally located opening for securing said needle holder wherein said needle holder can be installed from the front of the assembled device.

15. The combination of claim 14 wherein said centrally located opening is formed by a forwardly extending tubular wall which in cooperation with the hub serves to confine said biasing means between the hub and the retraction body.

16. The combination of claim 15 wherein the biasing means comprises a coil spring which closely circumscribes the tubular wall of the retraction body thereby stabilizing the retraction body as it retracts.

17. The combination of claim 10 wherein said cap is hingedly connected at the back of the outer body to pivot at the hinge between said open and said closed position thereby positioning said protrusion to engage the contact surface on the movable member to cause said forward movement of the movable member when the cap is moved to the closed position.

18. The combination of claim 17 wherein said cap has an outer rim larger than the opening in the back of the outer body and an inner rim comprising two camming protrusions which are spaced apart and positioned to enter said opening when the cap is moved to the closed position.

19. The combination of claim 18 wherein said protrusions are oppositely positioned along the inner rim about half-way from the hinged connection.

*20. A cap operated retractable medical device in combination comprising:*

*a tubular outer body having a front end portion, a back end portion and an open back end;*

*a movable cap disposed at the back end portion of the tubular outer body, the movable cap being movable from an open position to a closed position to close the open back end of the tubular outer body;*

*a needle bearing retraction body disposed in the tubular outer body and comprising a needle projecting outwardly from the front end portion; and*

*a movable member extending between the closed position and the retraction body, the movable member disengaged from the movable cap in its open position;*

*whereby the action of closing the cap causes initial engagement between the cap and the movable member, closes the open back end of the tubular outer body and causes the movable member to release the needle bearing retraction body, retracting the needle within the tubular outer body and retaining it therein.*

*21. The combination of claim 20 wherein the retraction body is retractably held by the movable member operated by the action of closing the cap.*

*22. The combination of claim 20 wherein the movable cap is normally open and movable from the normally open to the closed position.*

*23. The combination of claim 22 wherein the cap is hingedly supported at the back end of the tubular outer body for movement from the normally open to the closed position.*

*24. The combination of claim 20 wherein the needle bearing retraction body is retractably held by the movable member which moves in response to the action of closing said cap.*

*25. The combination of claim 24 wherein the movable member has a mouth having an inner surface which retractably holds the retraction body.*

*26. The combination of claim 25 wherein the needle bearing retraction body is retractably held within the mouth of the movable member by means of a sliding interference fit.*

*27. The combination of claim 24 wherein the front end portion of the tubular outer body has a hub which serves to release the retraction body from the moveable member as the moveable member moves in response to the action of closing the cap.*

*28. The combination of claim 24 wherein the movable member has an outer surface being slidingly held by means of the inner wall surface of the tubular outer body.*

*29. The combination of claim 24 wherein the movable member has an outer surface having a sliding interference fit with an interior surface portion of the front end portion of the tubular outer body which frictionally supports the moveable member with the exposed needle in an untreated condition.*

*30. The combination of claim 24 wherein the front portion of the tubular outer body has a hub with an opening for receiving a forward portion of the unretracted retraction body and a stop for the retraction body when the movable member moves in response to the action of closing said cap.*

*31. A cap operated retractable medical device, in combination comprising:* a hollow body having a front end portion and an open back end;

*a pivotably connected cap associated with the hollow body which closes the open back end of said body by the action of closing the cap;*

*a retractably mounted needle being releasably held in a pre-retraction position by a hollow movable member which is operated by the action of closing the cap to release the needle; and*

*the needle being retracted into the hollow movable member by the action of closing the cap, the needle being retained within said movable member thereby preventing needle sticks.*

*32. The combination of claim 31 wherein the movable member is a tubular member within the hollow body which is operated by the action of closing the cap.*

*33. The combination of claim 31 wherein the retractably mounted needle is mounted in a retraction body releasably held by the movable member.*

*34. The combination of claim 33 wherein the movable member is a tubular member having a front end portion and an open back end.*

*35. The combination of claim 34 wherein the retraction body is a discoid shaped member releasably held in the front end portion of the movable member.*

*36. The combination of claim 35 wherein the discoid shaped member has an outer edge which is releasably held by means for a sliding interference fit at the front end portion of the movable member.*

*37. The combination of claim 34 wherein the front end portion of the movable member is releasably held by means of a sliding interference fit at the front end portion of the hollow body.*

*38. A cap operated retractable medical device combination comprising:*

*a tubular outer body having a back end having an opening and a front end portion;*

*a cap mounted at the back end of the outer body for movement between an open position and a closed position relative to the opening at the back end of the outer body;*

*a movable member slidingly positioned in the tubular outer body, the movable member being responsive to movement of the cap from its open to its closed position;*

*a retraction body associated retractably with one end of the movable member; and*

*whereby the retraction body is dissociated from the movable member and retained in the tubular outer body by the act of moving the cap to its closed position.*

*39. A method of operating a retractable medical device, comprising the steps of:*

*providing a tubular outer body having a front end containing a retraction mechanism with a retractable needle and an open back end having a closeable cap attached by a hinge to the outer body;*

*retracting the needle by the action of closing the cap; and*

*retaining the retracted needle within the tubular outer body.*

*40. The method of claim 39 wherein the step of retracting the needle is performed by pressing the closeable cap against a movable member associated with the retractable needle.*

*41. The method of claim 40 wherein the retractable needle comprises a retraction body removably holding the needle, the retraction body being removably associated with the movable member and the step of pressing the closeable cap against the movable member includes the step of dissociating the retraction body from the movable member.*

*42. The method of claim 41 wherein the step of dissociating the retraction body from the movable member is accomplished by the steps of stopping the retraction body from moving forward while the movable member is moving forward in response to the step of pressing the closeable cap against the moveable member.*

*43. The method of claim 42 wherein the step of stopping the retraction body from moving forward while the movable member is moving forward is accomplished by the step of bringing the retraction body into contact with a structure in the front end of the tubular outer body.*

*44. The method of claim 42 wherein the step of stopping the retraction body from moving forward while the movable member is moving forward is accomplished by the step of slidingly separating an interface between the retraction body and the movable member.*

*45. In a medical device having a tubular outer body with an open end, a needle retraction body disposed opposite the open end, and a movable member slidably axially in the outer body, the improvement comprising a cap pivotably connected to the outer body to close the open end and thereby initiate retraction of a needle into the tubular outer body by operation of the retraction body.*

*46. The medical device of claim 45 wherein the movable member is disposed between the cap and the retraction body, the retraction body being releasable when the movable member is displaced by movement of the cap during closure of the open end of the tubular outer body.*

*47. The medical device of claim 45 wherein the medical device is a fluid collection device.*

*48. The medical device of claim 47 wherein the fluid collection device is a blood sampler.*

*49. In a medical device having a tubular outer body with an open end, a needle retraction body disposed opposite the open end, and a movable member slidably axially in the outer body, the improvement comprising a cap hinged to the outer body to close the open end and thereby initiate retraction of a needle into the tubular outer body by operation of the retraction body.*

*50. In a medical device having a tubular outer body with an open end, a needle retraction body disposed opposite the open end, and a movable member slidably axially in the outer body, the improvement comprising a cap unitarily molded to the outer body to close the open end and thereby initiate retraction of a needle into the tubular outer body by operation of the retraction body.*

*51. In a blood sampler having a tubular outer body with an open end, a needle retraction body disposed opposite the open end, and a movable member slidable axially in the outer body, the improvement comprising an end obstruction attached to the tubular outer body having a position independent of the movable member, the end obstruction initially contacting the movable member to move the movable member forward until retraction of a needle into the tubular outer body by operation of the retraction body.*

*52. In a blood sampler having a tubular outer body with an open end, a needle retraction body disposed opposite the open end, and a movable member slidable axially in the outer body, the improvement comprising a blocking member attached to the outer body adjacent its open end, the attached blocking member being selectively movable from a first position in which the blocking member does not traverse the open end to a second position in which the blocking member traverses the open end and also initiates retraction of a needle into the outer body by operation of the retraction body.*

*53. In a blood sampler having a tubular outer body with an open end, a needle retraction body disposed opposite the open end, and a movable member slidable axially relative to the outer body, the improvement comprising an end closure for the tubular outer body, the end closure having an open position providing access to the hollow interior of the movable member, a blocking position with respect to the open end that initiates contact with the movable member and a closed position preventing access to the hollow interior of the movable member and initiating retraction of a needle into the tubular outer body by operation of the retraction body.*

*54. The blood sampler of claim 53 wherein the end closure is attached to the outer body to close the open end of the outer body and also initiate retraction of a needle into the outer body by operation of the retraction body.*

*55. The blood sampler of claim 54 wherein the end closure is attached by a hinge to the outer body to close the open end and thereby initiate retraction of a needle into the tubular outer body by operation of the retraction body.*

*56. The blood sampler of claim 53 wherein the end closure is attached to the outer body to close the open end and thereby initiate retraction of a needle into the tubular outer body by operation of the retraction body, the end closure and outer body being unitarily molded.*

*57. The blood sampler of claim 53 wherein the movable member is disposed between the end closure and the retraction body, the retraction body being releasable when the movable member is displaced by movement of the end closure during closure of the open end of the tubular outer body.*

* * * * *

UNITED STATES PATENT AND TRADEMARK OFFICE

CERTIFICATE OF CORRECTION

PATENT NO. : RE 39,107 E
APPLICATION NO. : 09/665634
DATED : May 23, 2006
INVENTOR(S) : Shaw It is certified that error appears in the above-identified patent and that said Letters Patent is hereby corrected as shown below:

Col. 11, line 39, delete the word “untreated” and replace with --unretracted--.

Col. 13, line 3, delete the word “slidably” and replace with --slidable--.

Col. 13, line 18, delete the word “slidably” and replace with --slidable--.

Col. 13, line 26, delete the word “slidably” and replace with --slidable--.

Signed and Sealed this

Tenth Day of October, 2006

JON W. DUDAS
*Director of the United States Patent and Trademark Office*